US006368873B1

(12) United States Patent
Chang et al.

(10) Patent No.: US 6,368,873 B1
(45) Date of Patent: Apr. 9, 2002

(54) IDENTIFICATION OF HUMAN URINE FOR DRUG TESTING

(75) Inventors: Shong-Ho Chang, Rancho Santa Fe; Huiyan Guo; Trang Nguyen, both of San Diego; Ker-Kong Tung, Del Mar; Yun-Fei Wei, San Diego, all of CA (US)

(73) Assignee: Applied Biotech, Inc., San Diego, CA (US)

( * ) Notice: Subject to any disclaimer, the term of this patent is extended or adjusted under 35 U.S.C. 154(b) by 0 days.

(21) Appl. No.: 09/057,736

(22) Filed: Apr. 9, 1998

(51) Int. Cl.[7] .................. G01N 33/558; G01N 33/563; G01N 33/53; G01N 33/00
(52) U.S. Cl. .................. 436/514; 436/513; 436/2; 436/111; 435/5; 435/6; 435/7.1; 435/7.92; 435/7.93; 435/7.94
(58) Field of Search .................. 436/513, 514, 436/2, 111; 435/5, 6, 7.1, 7.92, 7.93, 7.94

(56) References Cited

U.S. PATENT DOCUMENTS

| 5,120,643 A | * | 6/1992 | Ching et al. |
| 5,252,496 A | * | 10/1993 | Kang et al. |
| 5,804,452 A | * | 9/1998 | Pronovost et al. ......... 436/514 |
| 5,955,370 A | * | 9/1999 | Kell .............................. 436/2 |

FOREIGN PATENT DOCUMENTS

GB          WO 88/08534       *  11/1988

OTHER PUBLICATIONS

Buechler et al., "Simultaneous Detection of Seven Drugs of Abuse by the Triage Panel for Drugs of Abuse," Clin. Chem. 38:1678–1684 (1992).
Engvall, E., "Enzyme Immunassay ELISA and EMIT," Methods in Enzymology 70:419–439.
Liu, Ray H. et al., "Handbook of Workplace Drug Testing," Chapter 7: Adulteration of Urine Specimens, AACC Press (1995).
Snowden and Hommel, "Antigen Detection Immunoassay Using Dipsticks and Colloidal Dyes," J. Immunol. Methods 140:57–65 (1991).
Uotila et al., "Two–site Sandwich Enzyme Immunoassay with Monoclonal Antibodies to Human Alpha–Fetoprotein," J. Immunol. Methods 42:11–15 (1981).
Harvey et al., IVD Technology 34–40 May/Jun. 1996 (not enclosed).

* cited by examiner

*Primary Examiner*—Long V. Le
*Assistant Examiner*—Padma Baskar
(74) *Attorney, Agent, or Firm*—Wood, Herron & Evans, LLP

(57) ABSTRACT

This invention features methods and kits for identifying human urine samples for forensic purposes.

4 Claims, 3 Drawing Sheets

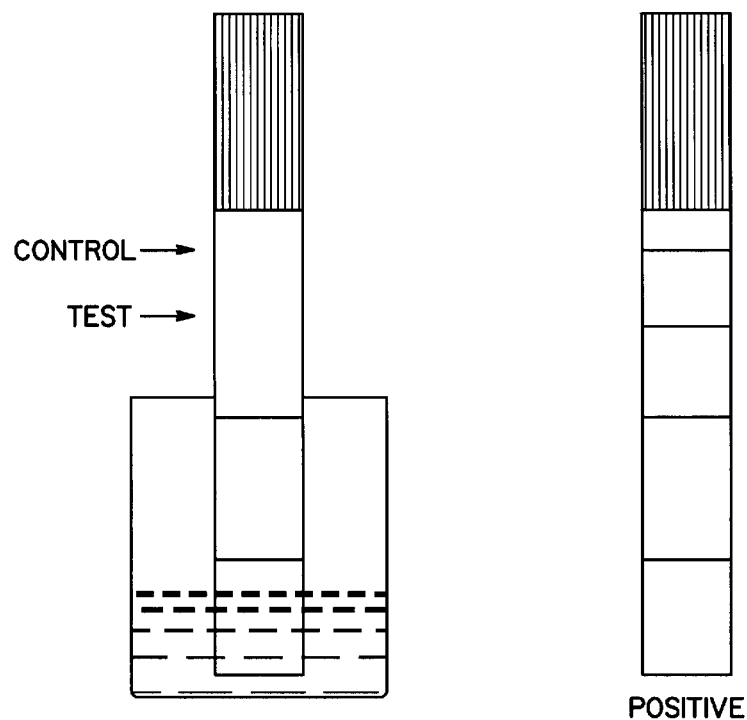
FIG. 3
FIG. 4 POSITIVE
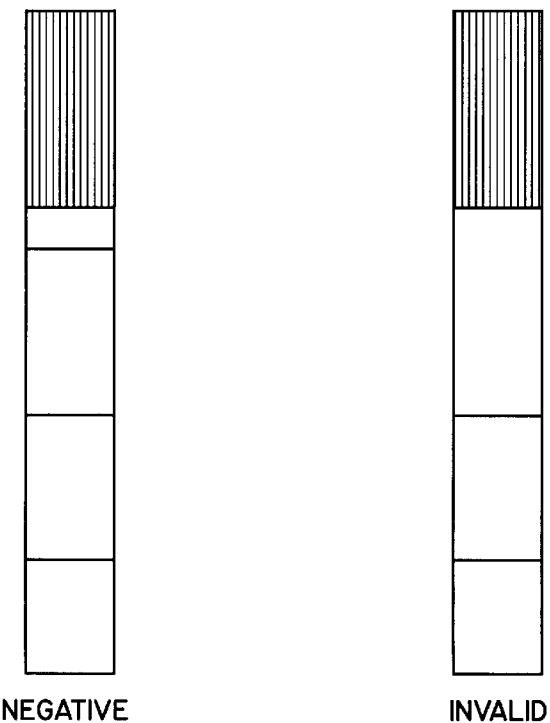
FIG. 5 NEGATIVE
FIG. 6 INVALID

IDENTIFICATION OF HUMAN URINE FOR DRUG TESTING

FIELD OF THE INVENTION

The present invention relates to forensic identification of human urine samples.

BACKGROUND OF THE INVENTION

Sample adulteration is a serious problem in forensic urine drug testing. Attempts to circumvent identification of drug abuse have led to the use of adulterants and substitutions in "urine" samples provided for drug testing (see Ray H. Liu & Bruce A. Goldberger, "Handbook of Workplace Drug Testing", AACC Press, 1995). For example, animal urine and non-urine liquid samples are often submitted as substitutes for human urine. For forensic purposes, it is important to positively identify human urine to the exclusion of substitute liquid samples.

Sample adulteration is usually achieved by substitution, dilution, or addition of adulterant into urine samples. The current methods for detecting sample adulteration test samples for pH, specific gravity, and creatinine concentration. However, the existence of a broad range of pH and specific gravity for urine samples limits the usefulness of these test results.

Creatinine is a normal constituent of urine (its concentration in the urine ranges from 15 to 300 mg per dl) and creatinine test is useful for identifying urine samples. However, it is difficult to use creatinine test to distinguish an animal sample from a human one because creatinine exists in both human and animal urine samples.

SUMMARY OF THE INVENTION

The present invention features a test kit and a simple, speedy and cost efficient method of identifying human urine samples. It allows for on-site identification of human urine samples without any equipment.

The test is a colloidal gold particle based Sandwich immunoassay for an antigen in human urine, e.g., human IgG, human IgA or human albumin. Because the test is specific for an antigen in human urine, it can positively identify a human urine sample to the exclusion of liquid substitutions. The sensitivity of this test also allows for the exclusion of grossly diluted human urine samples. In addition, this test can exclude human urine samples which have been so adulterated that the human antigen can no longer be detected.

Thus, this invention features a method of identifying or verifying a human urine sample with a test kit which has a chromatographic medium which contains (a) a collection of colored particles coated or otherwise attached with a first plurality of antibodies to a human antigen which exists in human urine, and (b) a first section containing a second plurality of antibodies to the same antigen. The colored particles are used as a visual marker for the test and include color and fluorescence particles known in the art, such as those described, disclosed or cited in U.S. Pat. No. 5,712,172, incorporated by reference herein in its entirety. Specifically, the colored particles include colloidal gold particles, colored latex, dye sols and carbon sols. In a preferred embodiment, colloidal gold particles are used. The antibody coated colloidal gold particles are capable of moving within the chromatographic medium by capillary action. The second plurality of antibodies is immobilized to the first section within the chromatographic medium. A test liquid sample is brought into contact with the chromatographic medium so as to move the colloidal gold particles by capillary action towards the first section. If the test liquid sample contains the antigen, the colloidal gold particles would aggregate in the first section in the form of antibody/antigen/antibody-coated colloidal gold particle Sandwiches. Such aggregation is observable by the formation of a colored band in the first section of the chromatographic medium. Therefore, the chromatographic medium is observed for the appearance of a colored band in the first section as an indication that the liquid sample is human urine.

By "chromatographic medium" is meant an absorptive material (preferably solid or semisolid) which, when brought into contact with a liquid, allows the flow of a mobile liquid phase over a stationary solid or semisolid phase. In addition, it allows the mobile liquid phase to carry colloidal gold particles in its movement over the stationary solid phase. The absorptive material is optionally deposited on or affixed to a nonabsorptive solid support (e.g., a strip of plastic). The absorptive material includes, but is not limited to, paper, membrane, pad, or a combination thereof. In a preferred embodiment, the membrane is selected from materials including, but not limited to, nitrocellulose, nylon and polyvinylidene bifluoride. In another preferred embodiment, the chromatographic medium comprises a strip of absorptive materials placed on a solid support and the strip of absorptive materials comprises a pad containing the colloidal gold particles and a membrane having a section precoated with antibodies to the antigen in human urine.

Colloidal gold particles have been used in diagnostic assays (Buechler et al., *Clin. Chem.* 38:1678–1684 (1992); Snowen and Hommel, *J. Immunol Methods* 140:57–66 (1991); and Harvey et al., *IVD Technology* 34–40, May/June (1996)). In a preferred embodiment, gold particles with a diameter of 5–100 nm are used in this invention. In a further preferred embodiment, gold particles with a diameter of 10–50 nm are used in this invention. In an even further preferred embodiment, gold particles with a diameter of 20–40 nm are used in this invention.

The antibodies attached to the colloidal gold particles and immobilized to the chromatographic medium may be polyclonal antibodies or monoclonal antibodies.

The antibodies can be attached to the gold particles by simple absorption or other means known to those skilled in the art, e.g., soaking the gold particles in an antibody solution. A gold sol pad can be made by soaking a pad in a suspension containing protein coated gold particles and allowing the wet pad to air-dry.

The antibodies can be attached to the membrane by airbrush spray technique or ink jet printing. The membrane is then allowed to air dry to immobilize the antibodies to a designated section.

A preferred antigen is one that is not present in animal urine samples, e.g., human IgG, human IgA or human albumin. In a further preferred embodiment, human IgG is the selected antigen.

In a preferred embodiment, the chromatographic medium contains a second collection of colloidal gold particles which are attached with a second antigen. The chromatographic medium also has a second section which contains antibodies to the second antigen and these antibodies are immobilized to the medium (alternatively, the gold particles are attached with the antibodies while the antigen is immobilized to the medium). When this second collection of colloidal gold particles move to the second section, they aggregate to form a second colored band because of the interaction between the second antigen and its antibody. The absence or presence of this second colored band can be used as an indication whether the chromatographic medium is defective. Preferably, the second antigen is not present in human urine samples, e.g., rabbit immunoglobulin G.

In another preferred embodiment, the chromatographic medium comprises a sample pad, a gold sol pad, a membrane, and optionally an absorbent pad (also called a sink pad) affixed to a strip of plastic support in that order. The plastic support is selected from materials including, but not limited to, polystyrene, polyester, and polyvinyl chloride (PVC). The sample pad is affixed to the support at one end of the strip for absorbing liquid test sample while the optional absorbent pad is at the other end of the strip. The absorbent pad is made of absorptive materials, including, but not limited to, paper for absorbing liquid from the membrane and facilitating capillary movement of the liquid sample and the gold particles. The gold sol pad is placed between the sample pad and the membrane and partially overlaps with both. The gold sol pad contains the colloidal gold particles. The membrane contains a first section with immobilized antibodies to the antigen in human urine and optionally a second section with immobilized antibodies to the second antigen.

Other features and advantages of the invention will be apparent from the following description of the preferred embodiments thereof, and from the claims.

BRIEF DESCRIPTION OF THE DRAWING

FIG. 3 is a drawing showing a test strip in use.

FIG. 4 is a drawing of the test strip of FIG. 3 indicating a postive result.

FIG. 5 is a drawing of the test strip of FIG. 3 indicating a negative result.

FIG. 6 is a drawing of the test strip of FIG. 3 indiciating an invalid result.

DETAILED DESCRIPTION OF THE INVENTION

Detecting Proteins in Human Urine Samples

Unadulterated human urine contains a small amount of proteins with a concentration of about 2–8 mg per 100 ml, including albumin, immunoglobulin A (IgA) and immunoglobulin G (IgG). For example, IgG is a normal constituent of urine sample at a concentration of 0.05 to 5 mg per 100 ml. Unlike creatinine, human IgG is present only in human bodily fluid but not in the urine of any other animals.

In order to verify that the tested urine samples have not been substituted, we have developed an immunoassay to detect specifically human protein IgA, IgG or albumin in urine.

The Surestep Urine Test is a qualitative, two-site sandwich immunoassay (Engvall, E., *Methods in Enzymology* 70:419–439, 1980; Uotila et al., *Immunol. Methods* 42:11, 1981) for the verification of human urine samples.

Figure 1:
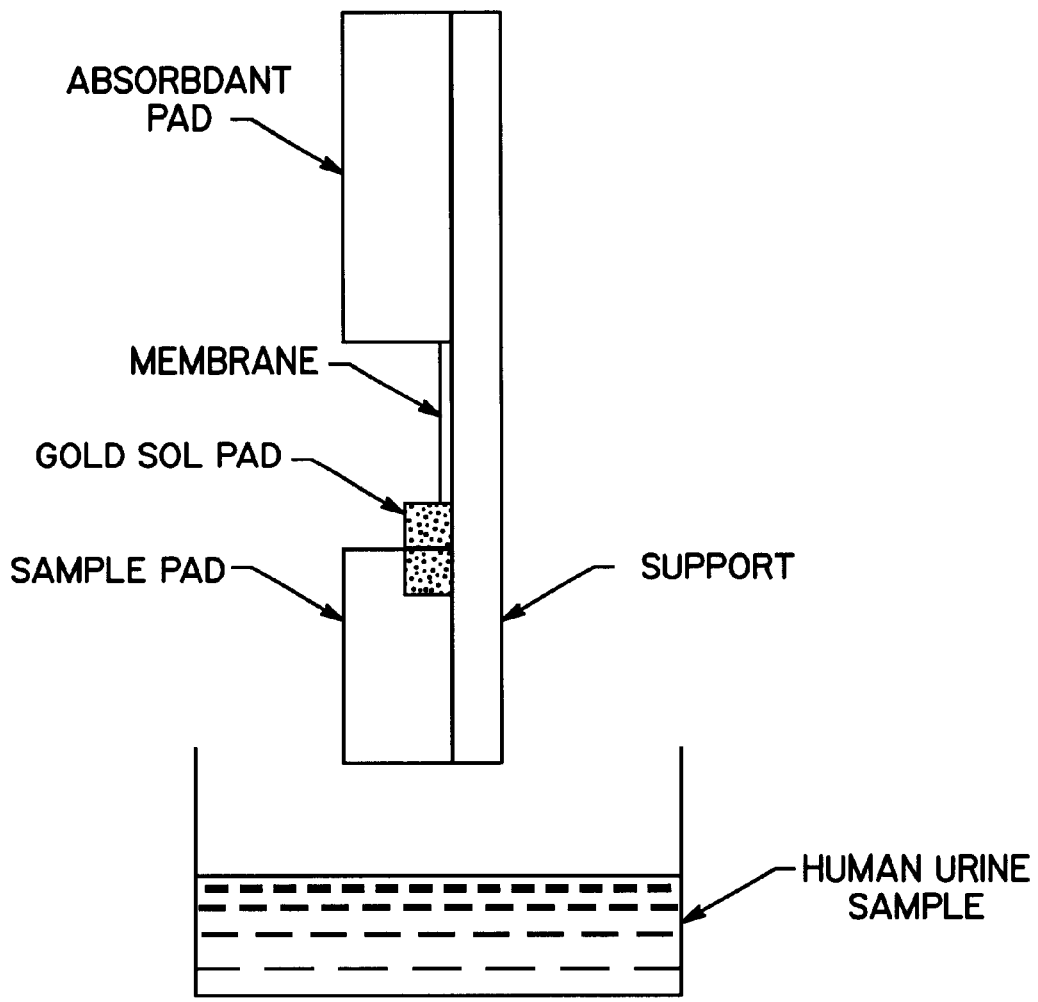
FIG. 1 is a cross-section view of a test strip for identifying human urine samples.
Figure 2:
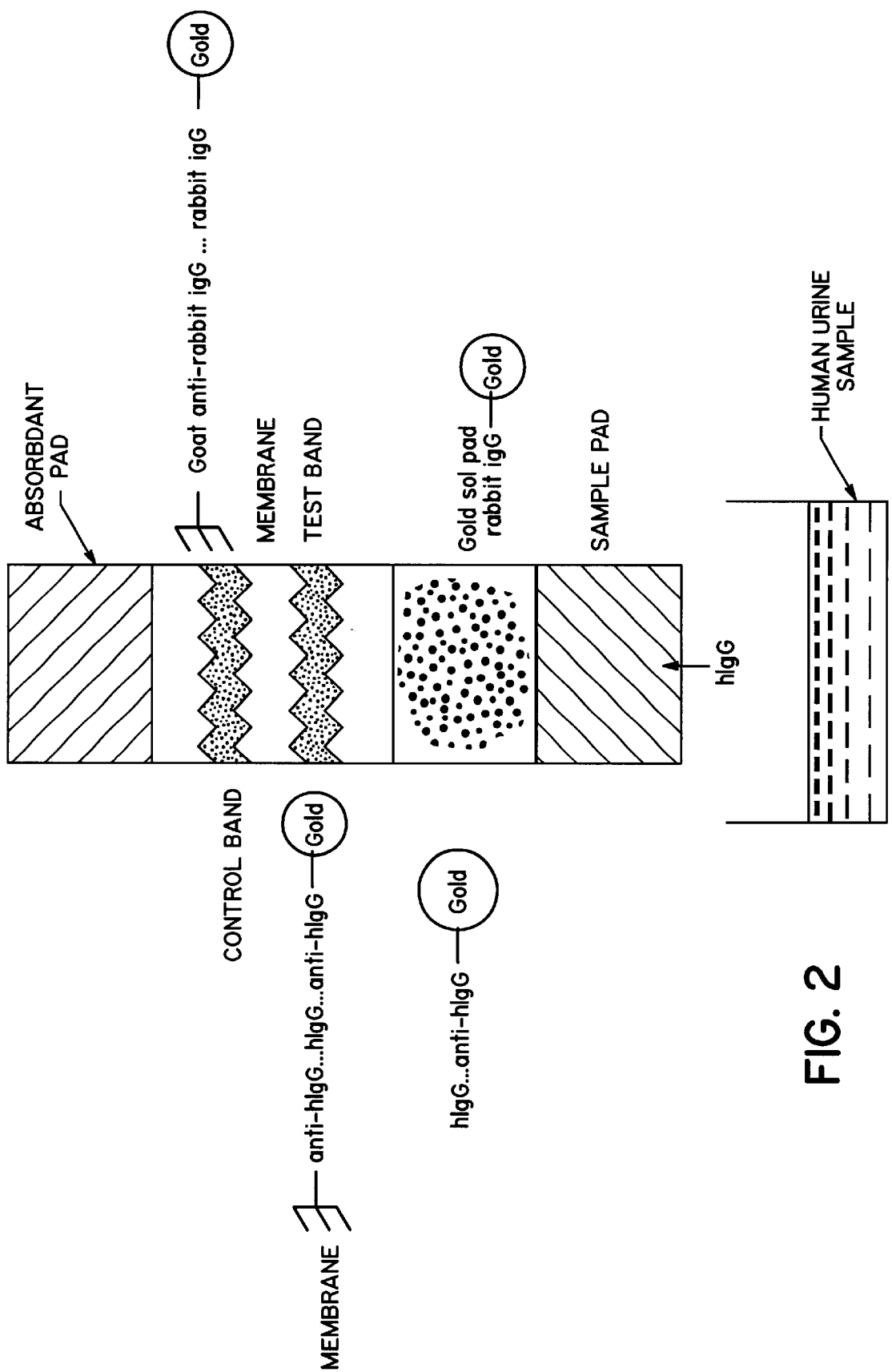
FIG. 2 is the front view of a test strip for identifying human urine samples.

FIGS. 1 and 2 illustrate the composition of a urine test strip and how it is used to identify human urine samples. The sample pad is for absorbing urine from a sample. The gold sol pad (also called gold conjugate pad) contains colloidal gold particles precoated with anti-human IgA, IgG or albumin. The membrane is coated with anti-human IgA, IgG or albumin in the test band region.

When a test strip is brought into contact with a human urine sample, human IgA, IgG or albumin in the urine specimen is reacted with the colloidal gold particles which have been coated with anti-human IgA, IgG or albumin. The antibody coated colloidal-gold-particles form immunocomplexes with the human antigen and move onto the membrane chromatographically by capillary action and migrate to the test band region which has been pre-coated with an antibody against human IgA, IgG or albumin. The immobilized antibody in the test band region captures the antigen/colloidal-gold-antibody complex and a colored band is formed on the membrane in the test band region. The absence of a colored band in the test band region indicates that the sample is not human urine.

In a preferred embodiment, the gold sol pad also contains colloidal gold particles precoated with a second antigen (preferably a nonhuman antigen) and the membrane is coated with an antibody against the second antigen in the control band region. A colored band would form in the control band region if the colloidal gold particles coated with the second antigen move onto the membrane by capillary action. A test strip is defective if no colored band is formed in the control band region. This test could detect human IgG at a concentration of 0.5 $\mu$g/ml or higher.

EXAMPLE 1

Immunoassay Kit for Human IgG in Urine Samples
Materials

A test strip contains a pre-coated membrane and a colloidal gold conjugate pad.

(1) Sample pad: Sample pad is treated with 6% tris buffer pH 8.5 with 3% S7 (Standapol ES-1) or other detergents which are capable of eliminate stain artifact caused by soft drinks.

(2) Colloidal gold conjugate: monoclonal anti-human IgG is coated with colloidal gold particles on the sample pad which is placed at the end of the membrane.

(3) Membrane: coated with monoclonal antibody to human IgG at a concentration of 2 mg/ml The test strip is supplied to users in a protective pouch.
Test Procedure
1. Remove the test strip from the protective pouch (bring the device to room temperature before opening the pouch to avoid condensation of moisture on the membrane).
2. Immerse the test strip in the urine sample. After a minimum of 15 seconds, remove the test strip from urine and lay flat on a non-absorptive clean surface.
3. Read result within 3–8 minutes after the addition of samples. Do not read result after 8 minutes.

The membrane is pre-coated with anti-hIgG capture antibody on the test band region and goat anti-rabbit IgG on the control band region. During testing, the urine specimen is allowed to react with the colored conjugate (mouse anti-hIgG monoclonal antibody—colloidal gold conjugate) which has been pre-dried on the test strip. The mixture then moves upward on the membrane chromatographically by capillary action. For a positive result, a pink-colored band with the specific antibody-hIgG-colored conjugate complex will form in the test band region of the membrane. Absence of this pink-colored band in the test band region suggests a negative result. Regardless of the presence of hIgG, as the mixture continues to move across the membrane to the immobilized goat antirabbit IgG, a pink-colored band at the control band region will always appear. The presence of this pink-colored band serves as: 1) verification that sufficient volume is added, 2) that proper flow is obtained, and 3) as a control for the reagents.

Interpretation of Results

FIG. 3 shows how to interpret the test results:

A. POSITIVE: Two distinct pink-colored bands will appear, one in the test band region and one in the control band region.

B. NEGATIVE: Only one pink-colored band appears in the control band region. No apparent pink band appears in the test band region.

C. INVALID: A total absence of pink-colored bands in both regions. If neither a test band nor a control band appears on the membrane, the test should be considered void. Improper testing procedures or deterioration of reagents probably occurred.

Results

A. Human Urine Samples

Seventy-five fresh urine samples from ABI employees showed positive results with Surestep Human Urine IgG Test.

B. Non-Human Urine Samples

Ten non-human urine samples from rabbit, goat, cow, and horse were tested and showed negative results, verifying that the urine samples were not sourced from a human.

C. Substitutions

The following non-urine liquid showed negative results with Surestep Human Urine IgG Test:

Deionized water, tap water, apple juice, orange juice, cranberry juice, grape juice, diet coke, Sprite, Root beer, Mountain dew, Pepsi, Squirt, tea, coffee, bleach, diluted detergent (2–10%), diluted liquid soap (5–20%), Drano, diluted Ethylene glycol (25–100%), alcoholic beverages, hydrogen peroxide (3% solution), diluted $NaHCO_3$ solution (2–8%), diluted NaOH solution (1%), diluted NaCl solution (5–20%), Lime-A-WAY <25%, and 1% Vanish.

All publications referenced are incorporated by reference herein, including drawings and sequences listed in each publication. All the compounds disclosed and referred to in the publications mentioned above are incorporated by reference herein, including those compounds disclosed and referred to in articles cited by the publications mentioned above. Other embodiments of this invention are disclosed in the following claims.

What is claimed is:

1. A method of screening to identify a sample submitted for drug testing as a human sample and thereafter testing said sample, comprising providing a urine sample for identification and performing an immunoassay on a chromatographic medium for detecting the presence of a single protein antigen present in human urine, said antigen selected from the group consisting of IgG, IgA, albumin, and combinations thereof using an antihuman IgG, IgA, or albumin antibody to identify said sample as a human sample, and thereafter performing drug testing.

2. The method of claim 1 wherein said immunoassay is an enzyme linked immunosorbent assay.

3. The method of claim 1 wherein said assay comprises (a) providing a chromatographic surface containing
  (i) a mobile signal-generating particle to which at least one antibody to said IgG, IgA or albumin protein is attached in a reaction section and
  (ii) at least one immobile antibody to said IgG, IgA or albumin is attached in a test section contacted by said sample after contact with said reaction section, (b) contacting said sample with said surface to react at said reaction section, and (c) thereafter determining if a signal is present in said test section.

4. The method of claim 3 wherein said reaction section further comprises a second mobile signal-generating particle to which at least one non-human protein as a control for defective chromatographic medium, improper test procedures, or the deterioration of reagents is attached and said test section further comprises at least a second immobile antibody to said non-human protein, and said detecting comprises comparing the presence of said signals generated from said human and said non-human proteins in said test section.

* * * * *